(12) United States Patent
Winter et al.

(10) Patent No.: US 12,239,939 B2
(45) Date of Patent: *Mar. 4, 2025

(54) METHODS AND APPARATUS FOR RECYCLING TAIL GAS IN SYNGAS FERMENTATION TO ETHANOL

(71) Applicant: LanzaTech, Inc., Skokie, IL (US)

(72) Inventors: John D. Winter, Houston, TX (US); Jerrod Hohman, Louisville, CO (US)

(73) Assignee: LanzaTech, Inc., Skokie, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/397,263

(22) Filed: Dec. 27, 2023

(65) Prior Publication Data

US 2024/0123401 A1    Apr. 18, 2024

Related U.S. Application Data

(63) Continuation of application No. 17/457,156, filed on Dec. 1, 2021, now Pat. No. 11,857,923, which is a
(Continued)

(51) Int. Cl.
*B01D 53/84* (2006.01)
*B01D 53/52* (2006.01)
(Continued)

(52) U.S. Cl.
CPC .............. *B01D 53/84* (2013.01); *B01D 53/52* (2013.01); *B01D 53/96* (2013.01); *C10J 3/482* (2013.01);
(Continued)

(58) Field of Classification Search
CPC ........ B01D 53/84; B01D 53/52; B01D 53/96; B01D 53/047; B01D 53/62; B01D 2251/95; B01D 2256/16; B01D 2256/20; B01D 2256/22; B01D 2257/504; B01D 2257/0916; C10J 3/482; C10J 3/723; C10J 2300/0916; C10J 2300/1618; C10J 2300/1621; C10J 2300/1665; C10J 2300/1823

See application file for complete search history.

(56) References Cited

U.S. PATENT DOCUMENTS 10,603,632 B2 *   3/2020   Winter ..................... C10J 3/482
11,202,989 B2 *  12/2021   Winter ..................... C12P 7/08
(Continued)

*Primary Examiner* — Michael L Hobbs

(57) ABSTRACT

The invention present provides a method (and suitable apparatus) to convert biomass to ethanol, comprising gasifying the biomass to produce raw syngas; feeding the raw syngas to an acid-gas removal unit to remove at least some $CO_2$ and produce a conditioned syngas stream; feeding the conditioned syngas stream to a fermentor to biologically convert the syngas to ethanol; capturing a tail gas from an exit of the fermentor, wherein the tail gas comprises at least $CO_2$ and unconverted CO or $H_2$; and recycling a first portion of the tail gas to the fermentor and/or a second portion of the tail gas to the acid-gas removal unit. This invention allows for increased syngas conversion to ethanol, improved process efficiency, and better overall biorefinery economics for conversion of biomass to ethanol.

23 Claims, 4 Drawing Sheets

Related U.S. Application Data continuation of application No. 16/751,981, filed on Jan. 24, 2020, now Pat. No. 11,202,989, which is a continuation of application No. 15/876,198, filed on Jan. 21, 2018, now Pat. No. 10,603,632.

(60) Provisional application No. 62/518,295, filed on Jun. 12, 2017.

(51) Int. Cl.

| | | |
|---|---|---|
| *B01D 53/96* | (2006.01) | |
| *C10J 3/48* | (2006.01) | |
| *C10J 3/72* | (2006.01) | |
| *C10K 1/00* | (2006.01) | |
| *C12P 7/08* | (2006.01) | |
| *B01D 53/047* | (2006.01) | |
| *B01D 53/62* | (2006.01) | |

(52) U.S. Cl.
CPC ............... *C10J 3/723* (2013.01); *C10K 1/005* (2013.01); *C12P 7/08* (2013.01); *B01D 53/047* (2013.01); *B01D 53/62* (2013.01); *B01D 2251/10* (2013.01); *B01D 2251/95* (2013.01); *B01D 2256/16* (2013.01); *B01D 2256/20* (2013.01); *B01D 2256/22* (2013.01); *B01D 2257/304* (2013.01); *C10J 2300/0916* (2013.01); *C10J 2300/1618* (2013.01); *C10J 2300/1621* (2013.01); *C10J 2300/1665* (2013.01); *C10J 2300/1823* (2013.01); *Y02E 50/10* (2013.01); *Y02P 20/145* (2015.11); *Y02P 20/151* (2015.11)

(56) References Cited

U.S. PATENT DOCUMENTS

| | | | |
|---|---|---|---|
| 11,857,923 B2* | 1/2024 | Winter | B01D 53/84 |
| 2009/0092524 A1* | 4/2009 | Ravikumar | C01B 17/0408 |
| | | | 422/171 |
| 2010/0251613 A1* | 10/2010 | Thacker | C10K 1/005 |
| | | | 48/197 R |
| 2011/0113676 A1* | 5/2011 | Mackay | C10K 1/007 |
| | | | 44/307 |

* cited by examiner

METHODS AND APPARATUS FOR RECYCLING TAIL GAS IN SYNGAS FERMENTATION TO ETHANOL

CROSS REFERENCE TO RELATED APPLICATIONS

This application is a continuation of U.S. patent application Ser. No. 17/457,156 filed Dec. 1, 2021, now U.S. Pat. No. 11,857,923, which is a continuation of U.S. patent application Ser. No. 16/751,981 filed Jan. 24, 2020, now U.S. Pat. No. 11,202,989, which is a continuation of U.S. patent application Ser. No. 15/876,198 filed Jan. 21, 2018, now U.S. Pat. No. 10,603,632, which claims the benefit of U.S. Provisional Patent Application 62/518,295 filed Jun. 12, 2017, all of which are incorporated herein by reference.

FIELD OF THE INVENTION

The present invention generally relates to the field of processes, process configurations, and apparatus for the conversion of synthesis gas to products, such as ethanol.

BACKGROUND OF THE INVENTION

Synthesis gas (hereinafter referred to as syngas) is a mixture of hydrogen ($H_2$) and carbon monoxide (CO). Syngas can be produced, in principle, from virtually any material containing carbon. Carbonaceous materials commonly include fossil resources such as natural gas, petroleum, coal, and lignite; and renewable resources such as lignocellulosic biomass and various carbon-rich waste materials. It is preferable to utilize a renewable resource to produce syngas because of the rising economic, environmental, and social costs associated with fossil resources.

Syngas is a platform intermediate in the chemical and biorefining industries and has a vast number of uses. Syngas can be converted into alkanes, olefins, oxygenates, and alcohols. These chemicals can be blended into, or used directly as, diesel fuel, gasoline, and other liquid fuels. Syngas can be converted to liquid fuels, for example, by methanol synthesis, mixed-alcohol synthesis, Fischer-Tropsch chemistry, and syngas fermentation to ethanol. Syngas can also be directly combusted to produce heat and power.

It is known that certain microorganisms can ferment combinations of carbon monoxide, hydrogen, and carbon dioxide to ethanol according to the following overall reactions:

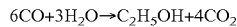

$$6CO + 3H_2O \rightarrow C_2H_5OH + 4CO_2$$

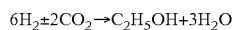

$$6H_2 \pm 2CO_2 \rightarrow C_2H_5OH + 3H_2O$$

Fermentation according to these reactions often employs anaerobic conditions. Depending on the organism and reaction conditions (e.g., pH), various other products can be produced, such as acetic acid, butyric acid, or butanol. Some strains of anaerobic microorganisms are reported to convert syngas to ethanol, n-butanol, or other chemicals with high selectivity.

Syngas fermentation to products such as ethanol and acetic acid can achieve fairly high selectivity, but due to mass-transfer limitations and low activities per unit volume of reactors, the reactors tend to be very large. Syngas conversion in well-mixed reactors is generally limited.

Additionally, production of ethanol from syngas will result in the co-formation of $CO_2$. This $CO_2$ is present in the tail gas of the fermentor, i.e. a vapor stream deriving from the fermentor. The tail gas generally contains any unconverted syngas, the $CO_2$ produced in the fermentation, and the inerts (including $CO_2$) initially contained in the syngas feed to the fermentor. The tail gas is commonly burned to recover the energy in the unconverted syngas as well as the energy in any other combustible components contained in the conditioned syngas stream, such as methane.

The unconverted syngas cannot simply be recycled to extinction. The inerts and the $CO_2$ produced in the fermentor must be removed from the overall process. Removal of $CO_2$ from the tail gas in a separate unit downstream of the fermentor is relatively expensive. Also, separation of the unconverted syngas from the inert gases and other species (such as methane) is not desirable.

In view of these problems associated with syngas fermentation, what is needed is an improved process configuration that more efficiently utilized syngas components to produce liquid products of interest, such as ethanol. Preferably, any such improvements do not cause significant increases in overall plant capital costs.

SUMMARY OF THE INVENTION

In some variations, the invention provides a method of converting a carbonaceous feedstock to a syngas-fermentation product, the method comprising:
  (a) introducing a carbonaceous feedstock and an oxidant to a gasifier, under suitable gasification conditions to produce a raw syngas stream comprising CO, $H_2$, and $CO_2$;
  (b) optionally feeding at least a portion of the raw syngas stream to a syngas-cleanup unit, to produce an intermediate syngas stream;
  (c) feeding at least a portion of the raw syngas stream and/or at least a portion of the intermediate syngas stream, if present, to an acid-gas removal unit, to remove at least some of the $CO_2$ and produce a conditioned syngas stream;
  (d) feeding at least a portion of the conditioned syngas stream to a fermentor, under suitable fermentation conditions and in the presence of suitable microorganisms and nutrients to biologically convert one or more of CO, $H_2$, or $CO_2$ to a syngas-fermentation product;
  (e) capturing a tail gas from an exit of the fermentor, wherein the tail gas comprises at least $CO_2$ and unconverted CO or $H_2$;
  (f) recycling a first amount of the tail gas to the fermentor in an amount described by $R_1$, the volumetric ratio of the first amount to the tail gas, wherein $R_1$ is selected from 0 to 1; and
  (g) recycling a second amount of the tail gas to the acid-gas removal unit in an amount described by $R_2$, the volumetric ratio of the second amount to the tail gas, wherein $R_2$ is selected from 0 to 1, wherein $R_1 + R_2$ is greater than 0; and wherein $R_1 + R_2$ is not greater than 1.

The carbonaceous feedstock may include, or consist essentially of, biomass. The oxidant may include one or more of air, oxygen, and steam. The gasifier is a fluidized-bed gasifier, in some embodiments.

In some embodiments, the method includes feeding at least a portion of the raw syngas stream to a syngas-cleanup unit, to produce an intermediate syngas stream. The acid-gas removal unit may be configured to additionally remove at least some $H_2S$, if present.

In some embodiments, the first amount of the tail gas is compressed before being recycled to the fermentor. In these or other embodiments, the second amount of the tail gas is compressed before being recycled to the acid-gas removal unit. Optionally, the first amount and the second amount of the tail gas are separately compressed before being recycled to the fermentor and the acid-gas removal unit, respectively.

In some embodiments, $R_1$ is selected from 0 to about 0.5, or from 0 to about 0.2. In some embodiments, $R_2$ is selected from 0 to about 0.8, or about 0.2 to about 0.5. In some embodiments, the sum $R_1+R_2$ is selected from about 0.001 to about 0.8, such as from about 0.25 to about 0.5.

The method may include a tail gas recycle control strategy to respond to one or more upstream parameters selected from the group consisting of feedstock type, oxidant profile, syngas-generation design or performance, syngas-cleanup design or performance, and acid-gas removal design or performance.

The method may include a tail gas recycle control strategy to respond to one or more fermentor parameters selected from the group consisting of temperature, pressure, residence time, pH, redox potential, nutrient concentration, cell viability, and cell vitality. Some embodiments further include recycling cells from the fermentor back to the gasifier.

The method may include a tail gas recycle control strategy to respond to one or more fermentor variables selected from the group consisting of CO conversion, $H_2$ conversion, $CO_2$ conversion, ethanol selectivity, ethanol productivity, ethanol titer, and acetic acid selectivity.

In certain embodiments, the method includes a tail gas recycle control strategy to control the $CO_2$ content in the feed to the fermentor. For example, the $CO_2$ content in the feed to the fermentor may be controlled to a level selected from about 5 vol % to about 50 vol %, such as about 10-40 vol % or about 20-30 vol % $CO_2$, by adjusting $R_1$ and/or $R_2$.

In certain embodiments, the method includes a tail gas recycle control strategy to control the acid gas molar ratio, $(CO+H_2)/(CO_2+H_2S)$, in the feed to the fermentor. For example, the acid gas molar ratio in the feed to the fermentor may be controlled to a value selected from about 2 to about 10 or more, or from about 10 to about 20.

In various embodiments, the tail gas contains between about 2% and about 10% of the syngas contained in the raw syngas stream. In some embodiments, tail gas recycle improves mass transfer within the fermentor. In these or other embodiments, compressed tail gas recycle increases the pressure within the fermentor, thereby allowing more syngas to enter the liquid phase for bioconversion.

A reformer may be disposed between the gasifier and the acid-gas removal step. The reformer may be utilized to convert or crack methane, tars, or other components, and produce additional syngas for bioconversion.

In some embodiments of the invention, the total conversion of CO and $H_2$ is at least 90%, more preferably at least 95%, and most preferably at least 98%. Other embodiments do not necessarily attempt to maximize syngas conversion, but rather optimize syngas conversion to products relative to plant energy needs.

In preferred embodiments, the total conversion of CO and $H_2$ is at least five percentage points higher than the total conversion of CO and $H_2$ that is attained in a comparable method with $R_1$ and $R_2$ both equal to 0. In more-preferred embodiments, the total conversion of CO and $H_2$ is at least ten or fifteen percentage points higher than the total conversion of CO and $H_2$ that is attained in a comparable method with $R_1$ and $R_2$ both equal to 0.

These methods may further include recovering the syngas-fermentation product from the fermentor. In some embodiments, the syngas-fermentation product is ethanol. The invention is, however, by no means limited to ethanol. Another exemplary syngas-fermentation product is butanol, such as 1-butanol.

Other variations of this invention provide an apparatus for converting a carbonaceous feedstock to a syngas-fermentation product, the apparatus comprising:
  (a) a gasifier for gasifying a carbonaceous feedstock with an oxidant, for producing a raw syngas stream comprising CO, Hz, and $CO_2$;
  (b) an optional syngas-cleanup unit in communication with the gasifier, for producing an intermediate syngas stream from at least a portion of the raw syngas stream;
  (c) an acid-gas removal unit in communication with the syngas-cleanup unit, if present; or in communication with the gasifier, if no syngas-cleanup unit is present; for removing at least some of the $CO_2$ and producing a conditioned syngas stream;
  (d) a fermentor in communication with the acid-gas removal unit, for biologically converting one or more of CO, $H_2$, or $CO_2$ to a syngas-fermentation product;
  (e) a tail gas conduit in communication with the fermentor; and
  (f) a recycle conduit in communication with the tail gas conduit for recycling tail gas to the fermentor.

Still other variations of this invention provide an apparatus for converting a carbonaceous feedstock to a syngas-fermentation product, the apparatus comprising:
  (a) a gasifier for gasifying a carbonaceous feedstock with an oxidant, for producing a raw syngas stream comprising CO, Hz, and $CO_2$;
  (b) an optional syngas-cleanup unit in communication with the gasifier, for producing an intermediate syngas stream from at least a portion of the raw syngas stream;
  (c) an acid-gas removal unit in communication with the syngas-cleanup unit, if present; or in communication with the gasifier, if no syngas-cleanup unit is present; for removing at least some of the $CO_2$ and producing a conditioned syngas stream;
  (d) a fermentor in communication with the acid-gas removal unit, for biologically converting one or more of CO, Hz, or $CO_2$ to a syngas-fermentation product;
  (e) a tail gas conduit in communication with the fermentor; and
  (f) a recycle conduit in communication with the tail gas conduit for recycling tail gas to the acid gas removal unit.

Yet other variations of this invention provide an apparatus for converting a carbonaceous feedstock to a syngas-fermentation product, the apparatus comprising:
  (a) a gasifier for gasifying a carbonaceous feedstock with an oxidant, for producing a raw syngas stream comprising CO, Hz, and $CO_2$;
  (b) an optional syngas-cleanup unit in communication with the gasifier, for producing an intermediate syngas stream from at least a portion of the raw syngas stream;
  (c) an acid-gas removal unit in communication with the syngas-cleanup unit, if present; or in communication with the gasifier, if no syngas-cleanup unit is present; for removing at least some of the $CO_2$ and producing a conditioned syngas stream;
  (d) a fermentor in communication with the acid-gas removal unit, for biologically converting one or more of CO, Hz, or $CO_2$ to a syngas-fermentation product;
  (e) a tail gas conduit in communication with the fermentor;

(f) a recycle conduit in communication with the tail gas conduit for recycling tail gas, wherein the recycle conduit includes a first conduit for recycling a first amount of the tail gas to the fermentor and a second conduit for recycling a second amount of the tail gas to the acid-gas removal unit.

The gasifier may be a fluidized-bed gasifier, for example. Some apparatus further include a reformer disposed between the gasifier and the acid-gas removal unit. Preferred apparatus include one or more compressors in communication with the recycle conduit. Some apparatus further include a purification unit for recovering, in purified form, the syngas-fermentation product from the fermentor.

The syngas-fermentation product may be ethanol, butanol, acetic acid, butyric acid, or any other biological products associated with production or growth of one or more microorganisms capable of consuming CO, Hz, and/or $CO_2$.

DETAILED DESCRIPTION OF EMBODIMENTS OF THE INVENTION

Figure 1:
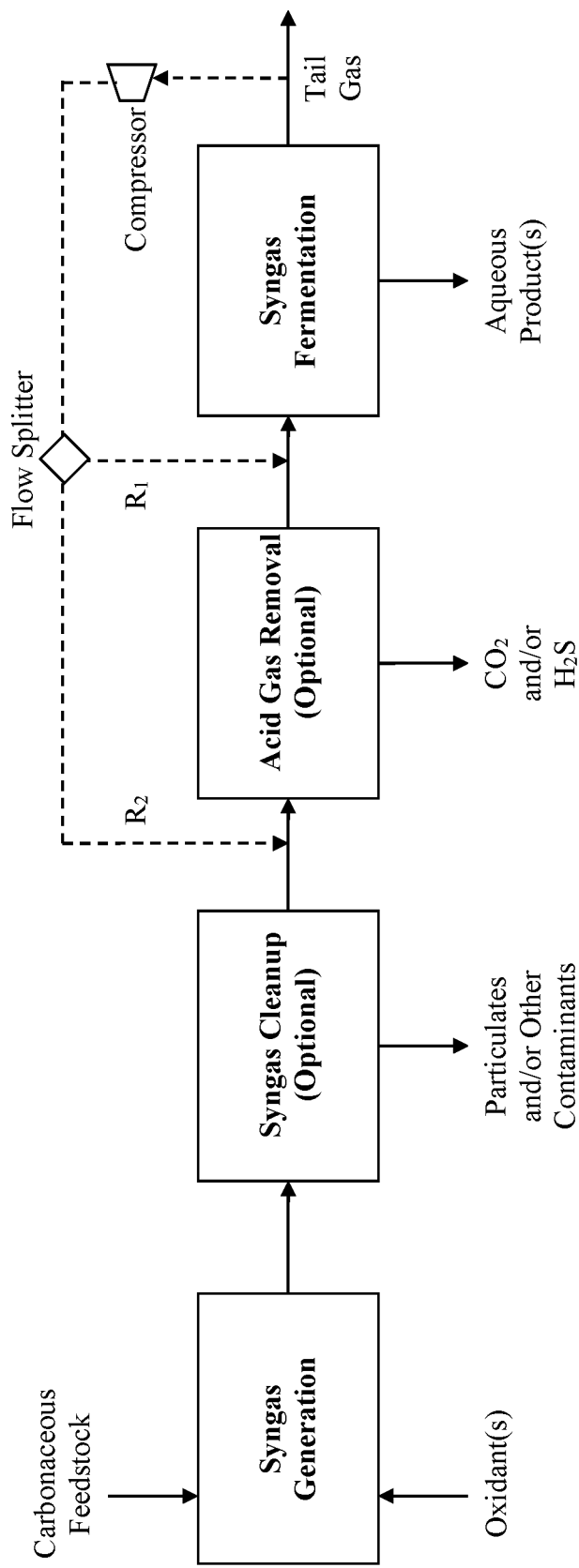
FIG. 1 is a block-flow diagram depicting some embodiments of the present invention.

This description will enable one skilled in the art to make and use the invention, and it describes several embodiments, adaptations, variations, alternatives, and uses of the invention, including what is presently believed to be the best mode of carrying out the invention.

As used in this specification and the appended claims, the singular forms "a," "an," and "the" include plural referents unless the context clearly indicates otherwise. For example, "a fermentor" includes a plurality of actual fermentors, in series or in parallel. Unless defined otherwise, all technical and scientific terms used herein have the same meaning as is commonly understood by one of ordinary skill in the art to which this invention belongs.

Unless otherwise indicated, all numbers expressing reaction conditions, stoichiometries, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

Some variations of the invention can be described by reference to the process configuration shown in FIG. 1, which relates to both apparatus and methods to carry out the invention. Any reference to a method "step" includes reference to an apparatus "unit" or equipment that is suitable to carry out the step, and vice-versa.

In the syngas-generation step, carbonaceous feedstock such as biomass is gasified with one or more oxidants to produce a raw syngas stream comprising at least syngas (CO and $H_2$). Other gas species in the raw syngas stream may include acid gases $CO_2$ and $H_2S$, relatively inert species such as $CH_4$ and $N_2$, and trace constituents such as tars, ash, and particulates.

The raw syngas stream from syngas generation may undergo one or more clean-up steps to remove specific contaminants, such as particulates, thereby forming an intermediate syngas stream. The raw syngas stream and/or the intermediate syngas stream (which may include some amount of recycle) optionally undergo an acid-gas removal step to remove bulk amounts of $CO_2$ and/or $H_2S$, thereby forming a conditioned syngas stream. Typically, at least $CO_2$ (and $H_2O$) will be removed in an acid-gas removal unit, but $H_2S$ removal may also be desired. Whether $H_2S$ should also be removed, and to what extent, typically depends on how much sulfur is present (if any) in the carbonaceous feedstock, the impact of sulfur-containing compounds on downstream operations, and the impact $H_2S$ removal may have on $CO_2$ removal.

The intermediate stream, upstream of the addition of a recycle stream (if any), will typically have between about 5-30 vol % $CO_2$. The conditioned syngas stream, upstream of the addition of a recycle stream (if any), will typically have between about 1-25 vol % $CO_2$, or 2-20 vol % $CO_2$ in some embodiments. The tail gas stream, in various recycle scenarios, will typically have between about 10-90 vol % $CO_2$, such as about 20-80 vol % $CO_2$, or about 25-75 vol % $CO_2$. Other ranges of $CO_2$ content in various streams are possible, depending on many factors.

The conditioned syngas stream is suitable for direct biological conversion processes, wherein microorganisms (such as the microorganisms described herein) directly convert one or more of $H_2$, CO, and $CO_2$ to ethanol, acetic acid, butyric acid, butanol, or another fermentation product. When tail gas comprising syngas is recycled, the syngas is given another pass for biological conversion to ethanol or another product.

In some variations, as depicted in FIG. 1, at least a portion of the tail gas may be recycled to the fermentor feed, or to a $CO_2$-removal step upstream of the fermentor feed, or to both of these locations. When a $CO_2$-removal unit is already in place, recycling to it is particularly advantageous because additional unit operations become unnecessary.

Some variations of the invention are premised on the realization that recycle streams can be tuned so that syngas generation and balance-of-plant capital per unit product produced may actually decrease. With continued reference to FIG. 1, $R_1$ is the ratio of tail gas recycle to the fermentor feed divided by the total tail gas flow, each on a volume basis. $R_2$ is the ratio of tail gas recycle to the acid-gas removal unit divided by the total tail gas flow, each on a volume basis.

Recycle ratios $R_1$ and $R_2$ are non-negative numbers from 0 to 1. The sum of $R_1+R_2$ cannot exceed unity. $R_1+R_2=1$ represents total recycle of the tail gas, while $R_1+R_2=0$ represents no recycle of the tail gas to either locations indicated in FIG. 1. By mass balance, the fraction of tail gas that is not recycled plus $R_1$ plus $R_2$ must equal 1.

$R_1$ may be selected from various values from 0 to about 1, preferably from 0 to about 0.5, and more preferably from 0 to about 0.2. $R_2$ may be selected from various values from 0 to about 1, preferably from about 0.2 to about 0.8, and more preferably from about 0.2 to about 0.5. The sum $R_1+R_2$ may be selected from various values greater than 0 (e.g., 0.001 or more) to about 1, preferably from about 0.2 to about 0.8, and more preferably from about 0.25 to about 0.5.

$R_1$ should not be equal or close to one at steady state, because total recycle of tail gas back to the fermentor will cause a buildup of $CO_2$, other inerts, and syngas. However, in certain dynamic situations or due to equipment problems (e.g., problems with the tail gas combustion unit), it is possible to recycle all of the tail gas back to the fermentor feed (R 1=1) for some amount of time.

$R_2$ should also generally not be equal or close to one at steady state, unless the acid-gas removal unit is functionally designed to also remove inerts (e.g., $CH_4$ or $N_2$) and anything else that must be purged somewhere from the system. Again, in certain dynamic situations, it is possible to allow total recycle of tail gas to the acid-gas removal unit from some amount of time. These dynamic situations could include downstream equipment problems, availability issues with feed streams in the process, fermentation issues (e.g., a stationary phase wherein syngas conversion drops significantly), and so on.

The recycle ratios $R_1$ and $R_2$ may be subjected to various means of dynamic or steady-state process control. As is known, many feedforward and feedback control strategies are possible. $R_1$ and $R_2$ may independently be set to control points for a desired steady state, or for a desired or known unsteady state. A person of skill in the art of process control will also understand that the ratio of $R_1$ to $R_2$, derivatives of $R_1$ and $R_2$ with time, the ratio of the time derivatives of $R_1$ and $R_2$, the derivatives of process variables (such as CO or $H_2$ conversion, or ethanol productivity) with $R_1$ and $R_2$, and so on, may be utilized in various control strategies.

The following are exemplary control examples only and should not be construed as limiting in any way, or as being related to any particular fundamentals being applied. These examples demonstrate that $R_1$ and/or $R_2$ can be set to vary over time or as a function of other conditions in the process.

In some embodiments, $R_1$ and/or $R_2$ are adjusted continuously, or at least dynamically (e.g., periodically or intermittently), in response to one or more upstream parameters such as feedstock type, oxidant profile, syngas-generation design or performance, syngas-cleanup design or performance, or acid-gas removal design or performance.

In some embodiments, $R_1$ and/or $R_2$ are adjusted continuously, or at least dynamically (e.g., periodically or intermittently), in response to one or more fermentor parameters such as temperature, pressure, residence time, pH, redox potential, nutrient concentration, microorganism viability or vitality, and so on.

In some embodiments, $R_1$ and/or $R_2$ are adjusted to one or more fermentor design or performance variables such as CO conversion, $H_2$ conversion, $CO_2$ conversion, ethanol selectivity, ethanol productivity, ethanol titer, or acetic acid selectivity. Such adjustment may be in combination with a response to fermentor parameter, such as those listed above.

Certain embodiments adjust $R_1$ and/or $R_2$ to change or optimize the $CO_2$ content in the fermentor feed. The $CO_2$ level in the fermentor feed can be varied, by adjusting $R_1$ and/or $R_2$, to about 5-50 vol % $CO_2$, such as about 10-40 vol % $CO_2$, or about 20-30 vol % $CO_2$. Certain embodiments increase $R_2$, relative to $R_1$, so that more $CO_2$ can be removed in the acid-gas removal step and decrease the $CO_2$ level in the fermentor feed.

Some embodiments adjust $R_1$ and/or $R_2$ to change or optimize the syngas to acid gas molar ratio, $(CO+H_2)/(CO_2+H_2S)$, at one or more points in the process. Certain, preferred embodiments adjust $R_1$ and/or $R_2$ to change or optimize the syngas to acid gas molar ratio, $(CO+H_2)/(CO_2+H_2S)$, in the feed stream entering the fermentor. The syngas to acid gas molar ratio entering the fermentor can be varied, by adjusting $R_1$ and/or $R_2$, between about 2 to about 10 or more, such as about 11, 12, 13, 14, 15, 16, 17, 18, 19, or 20.

The syngas feed to the fermentor is typically at a higher pressure than the tail gas pressure. The reason is that upstream operations (gasification and acid-gas removal) generally favor higher pressures compared to fermentation. For example, the feed pressure to the fermentor may be about 2-40 barg, while the pressure of the tail gas may be about 0.1-2 barg (usually not greater than 1 barg). In order to recycle a gas stream to an upstream point that is at higher pressure, the pressure of the gas stream being recycled needs to be raised. Rather than removing $CO_2$ from the tail gas, compressing the remainder, and then recycling it back to the fermentor, this invention contemplates recycling some portion of the tail gas and compressing it, without otherwise separating its components. That is, a "portion" of the tail gas stream in this context refers to a flow split only, by some flow-splitting means (e.g., valves)—not a component split by some separation means.

In FIG. 1, the recycled tail gas is compressed upstream of the $R_1/R_2$ split. In other embodiments, the recycled tail gas may be split into two or more recycle streams and then each of these streams compressed. While this adds some cost, it allows for adjusting the pressure increase in the recycle streams individually, if desired.

The amount of compression may be varied, but the pressure of a recycle stream should be at least raised to a pressure sufficient to allow its introduction into the stream(s) of interest. It is possible to compress the recycled tail gas, particularly when recycled back to the acid-gas removal unit, such that the pressure of the combined stream is actually increased. This would add operating costs but may improve the $CO_2$ removal.

In some embodiments, the conversion of syngas is about 90-98% (molar conversion of CO and $H_2$). The syngas conversion may be influenced by a number of factors, including the levels of inerts in the conditioned syngas stream, and the fermentor conditions, such as temperature, pH, mixing and mass transfer, the presence of competing microorganisms, and so on. In some embodiments, the syngas conversion is 90-98% upon recycling of tail gas as described herein, and less than 90% (such as only 75-85%) without tail gas recycling, all other factors being held constant. Preferably, syngas conversion is about 1, 2, 3, 4, 5, 6, 7, 8, 9, 10, 11, 12, 13, 14, 15 or more percentage points higher by implementing one or more of the recycle methods taught herein.

Higher overall syngas conversion will mean that the tail gas contains less of the syngas initially generated. In some embodiments with tail gas recycle, the tail gas contains about 2% to about 10% of the syngas contained in the raw syngas stream; whereas, without tail gas recycle ($R_1$, $R_2$=0), the tail gas contains about 10% to about 25% of the syngas contained in the raw syngas stream. The syngas concentration and energy content of the tail gas stream is not necessarily less when tail gas recycle is employed, because $CO_2$ can be removed from the acid-gas removal step. The non-recycled tail gas flow rate may be reduced, in some embodiments.

Higher syngas conversions will translate into higher yields of products of interest, such as ethanol, because product selectivity is not expected to decrease using these recycle strategies. Product selectivity may actually improve when less $CO_2$ is fed to the fermentor, further increasing product yield.

Figure 2:
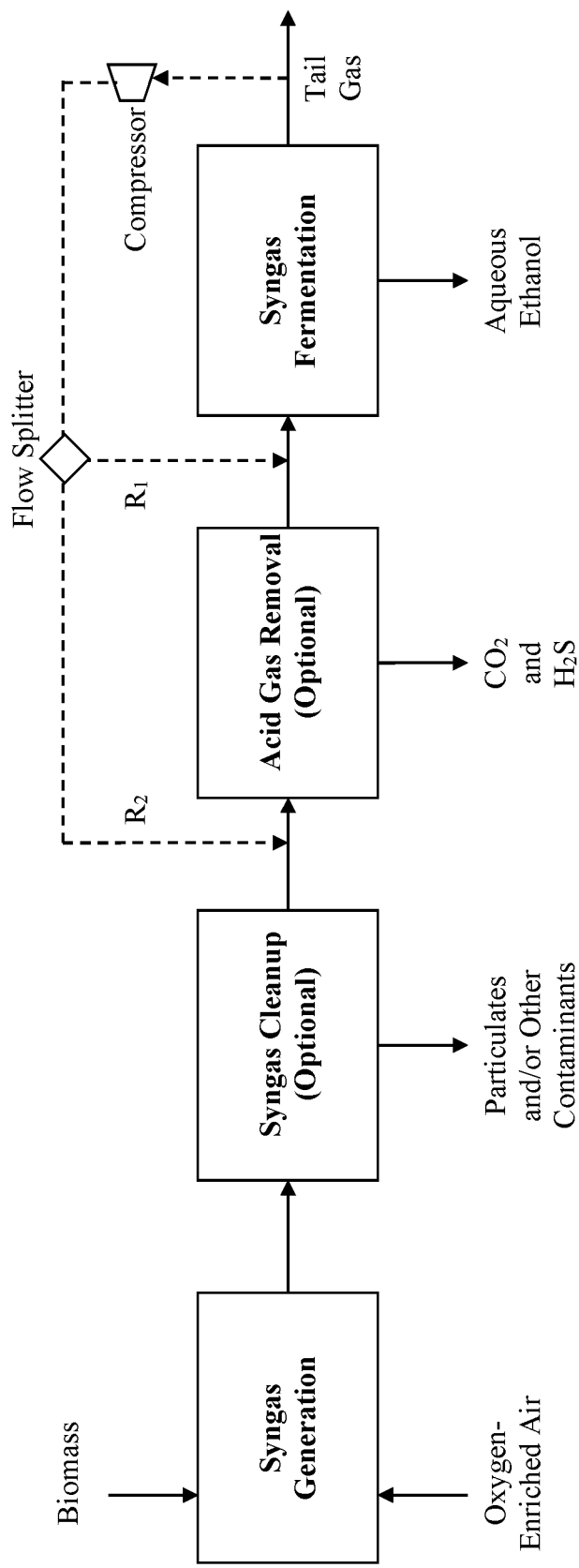
FIG. 2 is a block-flow diagram depicting some embodiments.
Figure 3:
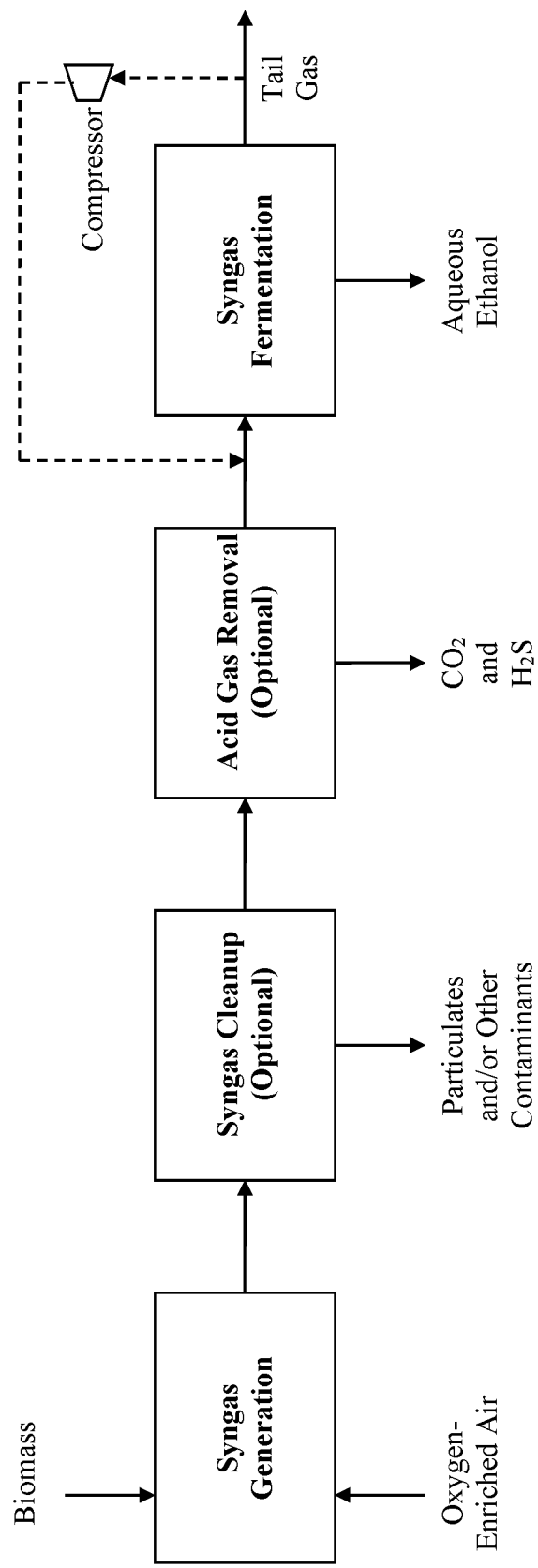
FIG. 3 is a block-flow diagram depicting certain embodiments.
Figure 4:
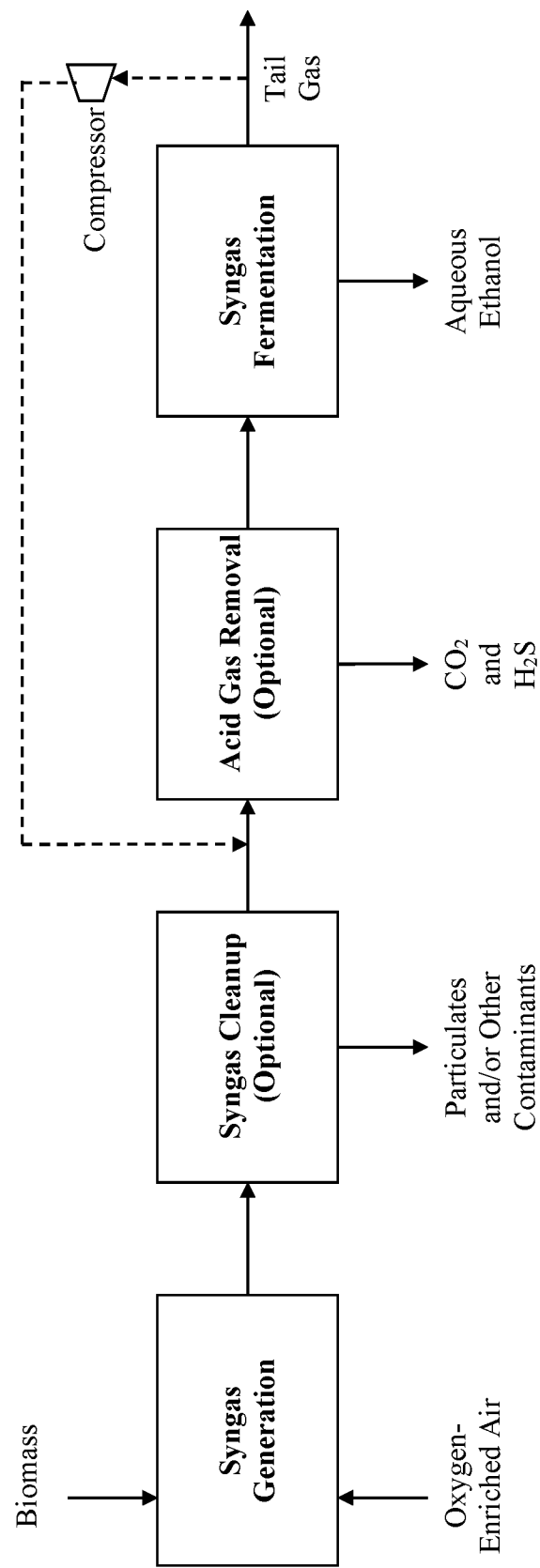
FIG. 4 is a block-flow diagram depicting some embodiments of this invention.

FIGS. 2-4 are provided to indicate other variations of the invention. In FIG. 2, the carbonaceous feedstock is biomass, the oxidant is oxygen-enriched air, and the product of interest is ethanol. In FIG. 3, there is recycle of some of the tail gas to the fermentor, but not any recycle to the acid-gas removal unit (R 2=0). In FIG. 4, there is recycle of some of the tail gas to the acid-gas removal unit, but not any recycle to the fermentor ($R_1$=0). All other aspects of these configurations may be selected or characterized as described with reference to FIG. 1 herein.

The syngas-generation unit or step may be selected from any known means, such as a gasifier. The gasifier could be, but is not limited to, a fluidized bed. Any known means for devolatilization or gasification can be employed. In variations, the gasifier type may be entrained-flow slagging, entrained flow non-slagging, transport, bubbling fluidized bed, circulating fluidized bed, or fixed bed. Some embodiments employ known gasification catalysts. "Gasification" and "devolatilization" generally refer herein to the reactive generation of a mixture of at least CO, $CO_2$, and $H_2$, using oxygen, air, and/or steam as the oxidant(s).

If gasification is incomplete, a solid stream can be generated, containing some of the carbon initially in the feed material. The solid stream produced from the gasification step can include ash, metals, unreacted char, and unreactive refractory tars and polymeric species. Generally speaking, feedstocks such as biomass contain non-volatile species, including silica and various metals, which are not readily released during pyrolysis, devolatilization, or gasification. It is of course possible to utilize ash-free feedstocks, in which case there should not be substantial quantities of ash in the solid stream from the gasification step.

When a fluidized-bed gasifier is employed as the devolatilization unit, the feedstock can be introduced into a bed of hot sand fluidized by a gas. Reference herein to "sand" shall also include similar, substantially inert materials, such as glass particles, recovered ash particles, and the like. High heat-transfer rates from fluidized sand can result in rapid heating of the feedstock. There can be some ablation by attrition with the sand particles. Heat is usually provided by heat-exchanger tubes through which hot combustion gas flows.

Circulating fluidized-bed reactors can be employed as the devolatilization unit, wherein gas, sand, and feedstock move together. Exemplary transport gases include recirculated product gas, combustion gas, or recycle gas. High heat-transfer rates from the sand ensure rapid heating of the feedstock, and ablation is expected to be stronger than with regular fluidized beds. A separator may be employed to separate the product gases from the sand and char particles. The sand particles can be reheated in a fluidized burner vessel and recycled to the reactor.

In some embodiments in which a countercurrent fixed-bed reactor is used as the gasifier, the reactor consists of a fixed bed of a feedstock through which a gasification agent (such as steam, oxygen, and/or recycle gas) flows in countercurrent configuration. The ash is either removed dry or as a slag.

In some embodiments in which a cocurrent fixed-bed reactor is used as the gasifier, the reactor is similar to the countercurrent type, but the gasification agent gas flows in cocurrent configuration with the feedstock. Heat is added to the upper part of the bed, either by combusting small amounts of the feedstock or from external heat sources. The produced gas leaves the reactor at a high temperature, and much of this heat is transferred to the gasification agent added in the top of the bed, resulting in good energy efficiency. Since tars pass through a hot bed of char in this configuration, tar levels are expected to be lower than when using the countercurrent type.

In some embodiments in which a fluidized-bed reactor is used as the gasifier, the feedstock is fluidized in recycle gas, oxygen, air, and/or steam. The ash is removed dry or as heavy agglomerates that defluidize. Recycle or subsequent combustion of solids can be used to increase conversion. Fluidized-bed reactors are useful for feedstocks that form highly corrosive ash that would damage the walls of slagging reactors.

The primary fluidizing agent for a fluidized-bed gasifier may be recycle gas, possibly including a portion of the fermentor tail gas. Due to the high heat-transfer characteristics of a fluidized bed, the recycle gas will cool and give up a portion of its sensible heat to the carbon-containing feedstock particles. Utilizing hot recycle gas to fluidize a bed of incoming biomass particles leads to improved overall energy efficiency.

In some embodiments in which an entrained-flow reactor is used as the gasifier, char is gasified with oxygen, air, or recycle gas in cocurrent flow. The gasification reactions take place in a dense cloud of very fine particles. High temperatures may be employed, thereby providing for low quantities of tar and methane in the product gas.

Entrained-flow reactors remove a major part of the ash as a slag, as the operating temperature is typically well above the ash fusion temperature. A smaller fraction of the ash is produced either as a very fine dry fly ash or as a fly-ash slurry. Some feedstocks, in particular certain types of biomass, can form slag that is corrosive. Certain entrained-bed reactors have an inner water- or steam-cooled wall covered with partially solidified slag.

In certain embodiments, the process configuration further includes a reformer disposed between the gasifier and the optional syngas-cleanup step or the acid-gas removal step. The reformer may be employed to convert or crack tars and methane to produce additional syngas, in some embodiments, optionally with a reforming catalyst.

The optional reformer, which can be regarded as within the syngas-generation unit of FIGS. 1-4, is any reactor capable of causing at least one chemical reaction that produces syngas. Conventional steam reformers, well-known in the art, may be used either with or without a catalyst. Other possibilities include autothermal reformers, partial-oxidation reactors, and multistage reactors that combine several reaction mechanisms (e.g., partial oxidation followed by water-gas shift). The reactor configuration may be a fixed bed, a fluidized bed, a plurality of microchannels, or some other configuration.

Heat can be supplied to the reformer reactor in many ways including, for example, by oxidation reactions resulting from oxygen added to the process. In some embodiments, a direct-fired partial-oxidation reactor is employed, wherein both oxygen and fuel are directly injected into the reactor to provide heat and assist in reforming and cracking reactions.

The reformer may include homogeneous (non-catalyzed) partial oxidation, catalytic partial oxidation, or both. Steam-reforming reactions may also be catalyzed. Reforming and/or partial-oxidation catalysts include, but are not limited to, nickel, nickel oxide, nickel alloys, rhodium, ruthenium, iridium, palladium, and platinum. Such catalysts may be coated or deposited onto one or more support materials, such as, for example, gamma-alumina (optionally doped with a stabilizing element such as magnesium, lanthanum, or barium).

When a reformer is employed, the gasifier chamber can be designed, by proper configuration of the freeboard or use of internal cyclones, to keep the carryover of solids to the downstream reformer at a level suitable for recovery of heat downstream of the reformer. Unreacted char can be drawn from the bottom of the devolatilization chamber, cooled, and then fed to a utility boiler to recover the remaining heating value of this stream.

The syngas-cleanup unit is not particularly limited in its design. Exemplary syngas-cleanup units include cyclones, centrifuges, filters, membranes, solvent-based systems, and other means of removing particulates and/or other specific contaminants.

The acid-gas removal unit is also not particularly limited, and may be any means known in the art for removing at least $CO_2$ from syngas. Examples include removal of $CO_2$ with one or more solvents for $CO_2$, or removal of $CO_2$ by a pressure-swing adsorption unit. Suitable solvents for reactive solvent-based acid gas removal include monoethanolamine, diethanolamine, methyldiethanolamine, diisopropylamine, and aminoethoxyethanol. Suitable solvents for physical solvent-based acid gas removal include dimethyl ethers of polyethylene glycol (such as in the Selexol® process) and refrigerated methanol (such as in the Rectisol® process).

Bioconversion of CO or $H_2/CO_2$ to acetic acid, ethanol, or other products is well known. For example, syngas biochemical pathways and energetics of such bioconversions are summarized by Das and Ljungdahl, "Electron Transport System in Acetogens" and by Drake and Kusel, "Diverse Physiologic Potential of Acetogens," appearing respectively as Chapters 14 and 13 of *Biochemistry and Physiology of Anaerobic Bacteria*, L. G. Ljungdahl eds., Springer (2003).

Any suitable microorganisms may be utilized that have the ability to convert CO, $H_2$, or $CO_2$, individually or in combination with each other or with other components that are typically present in syngas. The ability of microorganisms to grow on CO as their sole carbon source was first discovered over one hundred years ago. A large number of anaerobic organisms including carboxydotrophic, photosynthetic, methanogenic, and acetogenic organisms have been shown to metabolize CO to various end products.

Anaerobic bacteria, such as those from the genus *Clostridium*, have been demonstrated to produce ethanol from CO, $H_2$, or $CO_2$ via the acetyl CoA biochemical pathway. For example, various strains of *Clostridium ljungdahlii* that produce ethanol from gases are described in U.S. Pat. Nos. 5,173,429, 5,593,886, and 6,368,819. The bacterium *Clostridium autoethanogenum* sp is also known to produce ethanol from gases (Aribini et al., Archives of Microbiology 161, pp. 345-351 (1994)).

Generally speaking, microorganisms suitable for syngas fermentation in the context of the present invention may be selected from many genera including *Clostridium, Moorella, Carboxydothermus*, Acetogenium, Acetobacterium, Butyribacterium, *Peptostreptococcus*, and Geobacter. Microorganism species suitable for syngas fermentation in this invention may be selected from *Clostridium ljungdahlii, Clostridium autoethanogenum, Clostridium ragsdalei, Clostridium carboxidivorans, Butyribacterium methylotrophicum, Eubacterium limosum*, and genetically engineered, mutated, or evolved variations thereof. Microorganisms that are engineered, created, or provided in the future will be applicable to the present invention, provided such new microorganisms can convert one or more of CO, $H_2$, or $CO_2$ to a product of interest.

A selected microorganism may be grown, to at least some extent, in the fermentor itself (simultaneous growth and production) or may be grown in a separate growth vessel or train. When separate cell growth is utilized, microorganism cells can be grown from any carbon substrate, which could be syngas but also could be various sugars such as glucose, galactose, arabinose, xylose, mannose, and other $C_5$ or $C_6$ sugars.

The fermentor, or plurality of fermentors (in series or parallel), is not particularly limited but will generally be selected from a mechanically agitated reactor, a bubble column, a packed column, a plate column, a spray column, a gas-lift reactor, and a membrane reactor. In some embodiments, gas or liquid internal recycle is utilized to add mass transfer within the fermentor. Surfactants, water co-solvents, and microbubbles may all be utilized in various embodiments to enhance mixing and mass transfer.

In certain embodiments, tail gas recycle improves mass transfer within the fermentor. In certain embodiments, compressed tail gas recycle increases the pressure within the fermentor, thereby allowing more syngas to enter the liquid phase for bioconversion.

Some embodiments employ cell recycle back to the fermentor. Some embodiments employ recycle of cells, or fermentation sludge, back to the gasifier. Sludge recycling allows for conversion of used microorganisms back to syngas.

The mechanical art necessary for implementing the tail gas recycle streams is well established. With reference to FIG. 1, which is non-limiting, what is needed is a flow splitter in the tail gas stream, at least one compressor, a flow splitter to adjust $R_1$ and $R_2$, and appropriate pipes and valves.

The compressor is not limited but should be a mechanical device that increases the pressure of the tail gas by reducing its volume. Suitable compressors include centrifugal compressors, diagonal compressors, axial-flow compressors, reciprocating compressors, rotary screw compressors, rotary vane compressors, scroll compressors, and diaphragm compressors.

The methods and apparatus of the invention can accommodate a wide range of feedstocks of various types, sizes, and moisture contents. "Biomass," for the purposes of the present invention, is any material not derived from fossil resources and comprising at least carbon, hydrogen, and oxygen. Biomass includes, for example, plant and plant-derived material, vegetation, agricultural waste, forestry waste, wood waste, paper waste, animal-derived waste, poultry-derived waste, and municipal solid waste. Other exemplary feedstocks include cellulose, hydrocarbons, carbohydrates or derivatives thereof, and charcoal.

In various embodiments of the invention utilizing biomass, the biomass feedstock can include one or more materials selected from: timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, *miscanthus*, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth.

The present invention can also be used for carbon-containing feedstocks other than biomass, such as a fossil fuel (e.g., coal or petroleum coke), or any mixtures of biomass and fossil fuels. For the avoidance of doubt, any method, apparatus, or system described herein can be used with any carbonaceous feedstock.

Selection of a particular feedstock or feedstocks is not regarded as technically critical, but is carried out in a manner that tends to favor an economical process. Typically, regardless of the feedstocks chosen, there is screening to remove undesirable materials. The feedstock can optionally be dried prior to processing. Optionally, particle-size reduction can be employed prior to conversion of the feedstock to syngas. Particle size is not, however, regarded as critical to the invention.

When multiple feedstocks are used (e.g., biomass-coal mixtures), they may be used in any ratio and they may be introduced in the same or different locations. It will be understood that the specific selection of feedstock ratios can be influenced by many factors, including economics (feedstock prices and availability), process optimization (depending on feedstock composition profiles), utility optimization, equipment optimization, and so on.

A variety of operating temperatures, pressures, flow rates, and residence times can be employed for each unit operation of FIGS. 1-4 or other variations of the invention. As is known to a skilled artisan, the optimum conditions for each unit will be influenced by the conditions of other units.

Some embodiments of the invention relate to integration with the plant energy balance. The recycle loop(s) as described may be implemented to control the conversion of syngas to ethanol, adjusting for a steady-state or dynamic energy demand for syngas as an energy source. This invention allows real-time adjustment of how syngas is utilized in the overall process, thereby enhancing plant efficiency and economics.

In general, solid, liquid, and gas streams produced or existing within the process can be independently passed to subsequent steps or removed/purged from the process at any point. Also, any of the streams or materials present may be subjected to additional processing, including heat addition or removal, mass addition or removal, mixing, various measurements and sampling, and so forth.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

All publications, patents, and patent applications cited in this specification are herein incorporated by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent will cover those variations as well. The present invention shall only be limited by what is claimed.

What is claimed is:

1. A method of converting a carbonaceous feedstock to a syngas-fermentation product, said method comprising:
   a) passing the carbonaceous feedstock and an oxidant to a gasifier to gasify the feedstock and produce a raw syngas stream comprising CO, $H_2$, and $CO_2$;
   b) passing the raw syngas stream to a syngas cleanup unit to produce a first treated syngas stream, wherein the cleanup unit is selected from a cyclone, a centrifuge, a filter, a membrane, and a solvent-based system;
   c) feeding at least a portion of said first treated syngas stream to an acid-gas removal unit selected from a solvent removal unit or a pressure-swing adsorption (PSA) removal unit, to remove at least some of said $CO_2$ and produce a conditioned syngas stream;
   d) feeding at least a portion of said conditioned syngas stream to a fermentor, under suitable fermentation conditions and in the presence of suitable microorganisms and nutrients to biologically convert one or more of CO, $H_2$, or $CO_2$ to a fermentation product and generate a product stream comprising at least the fermentation product and a tail gas stream comprising at least $CO_2$ and unconverted CO and/or $H_2$; and
   e) recycling at least a first portion of the tail gas to the fermentor, at least a second portion of the tail gas to the acid-gas removal unit, or both.

2. The method of claim 1 wherein the gasifier further comprises a gasification catalyst.

3. The method of claim 1 wherein the cleanup unit is a cyclone or a filter.

4. The method of claim 1 further comprising cooling the first treated syngas stream prior to feeding it to the acid-gas removal unit.

5. The method of claim 1 wherein the acid-gas removal unit is a PSA removal unit.

6. The method of claim 1 further comprising drying the carbonaceous feedstock prior to passing it to the gasifier.

7. The method of claim 1 wherein no tail gas is recycled to the fermentor for a period of time or no tail gas is recycled to the acid-gas removal unit for a period of time.

8. The method of claim 1, wherein said carbonaceous feedstock comprises biomass, fossil fuels, or any combination thereof.

9. The method of claim 1, wherein said oxidant comprises one or more of air, oxygen, and steam.

10. The method of claim 1, wherein said gasifier is a fluidized-bed gasifier, bubbling fluidized bed gasifier, a circulating fluidized bed gasifier, a fixed bed gasifier, an entrained-flow slagging gasifier, entrained flow non-slagging gasifier, or a transport gasifier.

11. The method of claim 1, further comprising conducting measurements on the tail gas exiting the fermentor and controlling the amounts the first portion of the tail gas recycled to the fermentor and the second portion of the tail gas recycled to the acid-gas removal unit to control the $CO_2$ content in the feed to said fermentor.

12. The method of claim 11 wherein the $CO_2$ content in the feed to the fermentor varies from about 5 vol % to about 50 vol %.

13. The method of claim 1, wherein said acid-gas removal unit additionally removes at least some $H_2S$, if present.

14. The method of claim 1, further comprising compressing the first portion of the tail gas recycled to the fermentor, the second portion of the tail gas recycled to the acid-gas removal unit, or both.

15. The method of claim 1, further comprising controlling the amounts the first portion of the tail gas recycled to the fermentor and the second portion of the tail gas recycled to the acid-gas removal unit based on one or more upstream parameters selected from feedstock type, oxidant profile, syngas-generation design or performance, syngas-cleanup design or performance, acid-gas removal design or performance.

16. The method of claim 1, further comprising controlling the amounts the first portion of the tail gas recycled to the fermentor and the second portion of the tail gas recycled to the acid-gas removal unit based on one or more fermentor parameters selected from temperature, pressure, residence time, pH, redox potential, nutrient concentration, cell viability, and cell vitality.

17. The method of claim 1, further comprising controlling the amounts the first portion of the tail gas recycled to the fermentor and the second portion of the tail gas recycled to the acid-gas removal unit based on one or more fermentor variables selected from the group consisting of CO conversion, $H_2$ conversion, $CO_2$ conversion, ethanol selectivity, ethanol productivity, ethanol titer, and acetic acid selectivity.

18. The method of claim 1, further comprising controlling the amounts the first portion of the tail gas recycled to the fermentor and the second portion of the tail gas recycled to the acid-gas removal unit to control the acid gas molar ratio, $(CO+H_2)/(CO_2+H_2S)$, in the feed to said fermentor.

19. The method of claim 1, further comprising compressing the first portion of the tail gas recycled to the fermentor, the second portion of the tail gas recycled to the acid-gas removal unit, or both to increase the pressure within said fermentor and increase the amount of syngas entering the liquid phase for bioconversion.

20. The method of claim 1, further comprising a reformer disposed between said gasifier and said acid-gas removal step.

21. The method of claim 1, further comprising recycling cells from said fermentor back to said fermentor, said gasifier, or both.

22. The method of claim 1, further comprising recovering at least one product from the product stream.

23. The method of claim 22, wherein the at least one product is selected from the group consisting of ethanol, butanol, butyric acid, acetic acid, and any combination thereof.

* * * * *